(12) United States Patent
Caruhel et al.

(10) Patent No.: US 11,719,697 B2
(45) Date of Patent: *Aug. 8, 2023

(54) IMMUNOASSAY AND ANTIBODIES FOR THE DETECTION OF CHROMOGRANIN A

(71) Applicant: CEZANNE S.A.S., Nimes (FR)

(72) Inventors: Pascaline Caruhel, Nimes (FR);
Valerie Rigault, Roquemaure (FR);
Nadine Guerin, Bagnols sur Ceze (FR)

(73) Assignee: Cezanne S.A.S., Nimes (FR)

( * ) Notice: Subject to any disclaimer, the term of this patent is extended or adjusted under 35 U.S.C. 154(b) by 229 days.

This patent is subject to a terminal disclaimer.

(21) Appl. No.: 16/842,666

(22) Filed: Apr. 7, 2020

(65) Prior Publication Data
US 2020/0348304 A1   Nov. 5, 2020

Related U.S. Application Data

(63) Continuation of application No. 15/303,521, filed as application No. PCT/EP2015/058045 on Apr. 14, 2015, now Pat. No. 10,648,984.

(30) Foreign Application Priority Data

Apr. 15, 2014  (EP) .................................... 14164809

(51) Int. Cl.
| G01N 33/574 | (2006.01) |
| G01N 33/577 | (2006.01) |
| G01N 33/58 | (2006.01) |
| C07K 16/18 | (2006.01) |
| C07K 16/30 | (2006.01) |

(52) U.S. Cl.
CPC ......... *G01N 33/5748* (2013.01); *C07K 16/18* (2013.01); *C07K 16/30* (2013.01); *G01N 33/577* (2013.01); *G01N 33/582* (2013.01); *C07K 2317/34* (2013.01)

(58) Field of Classification Search
CPC ............. G01N 33/5748; G01N 33/577; G01N 33/582; G01N 2800/048; G01N 2800/342; G01N 2800/52; C07K 16/18; C07K 16/30; C07K 16/3069; C07K 2317/34
See application file for complete search history.

(56) References Cited

U.S. PATENT DOCUMENTS

| 6,238,877 B1 | 5/2001 | Wu et al. |
| 6,632,624 B1 | 10/2003 | Degorce et al. |
| 8,603,765 B2 | 12/2013 | Tacha |
| 2019/0086419 A1 | 3/2019 | Jardin-Watelet et al. |

FOREIGN PATENT DOCUMENTS

| EP | 2383293 A1 | 11/2011 |
| JP | 2002-514766 A | 5/2002 |
| WO | 99/58980 A1 | 11/1999 |
| WO | 2011/135035 A1 | 11/2011 |
| WO | 2012/065025 A2 | 5/2012 |
| WO | 2013/070088 A1 | 5/2013 |
| WO | 2013/070089 A1 | 5/2013 |

OTHER PUBLICATIONS

Edwards BM et al. The remarkable flexibility of the human antibody repertoire; isolation of over one thousand different antibodies to a single protein, BLyS. J. Mol. Biol. 2003, 334:103-118. (Year: 2003).*
International Search Report of International Patent Application No. PCT/EP2015/058045 dated Jun. 26, 2015.
Hogg, Robert Bernard, "A Processing Independent Analyses of Chromogranin A", PhD Thesis, Jan. 1, 1998, Queen's University of Belfast, Belfast, United Kingdom.
Hogg, Robert B. et al., "Immunological Studies Employing Antisera Generated to Residues 120-143 of Bovine Chromogranin A", Regulatory Peptides, Jul. 15, 1996, p. 71, vol. 64, No. 1-3.
Norlen, Per et al., "Cell-specific Processing of Chromogranin A in Endocrine Cells of the Rat Stomach", Journal of Histochemistry & Cytochemistry, Jan. 1, 2001, pp. 9-18, vol. 49, No. 1.
Portela-Gomes, Guida Maria et al., "Selective Processing of Chromogranin A in the Different Islet Cells in Human Pancreas", Journal of Histochemistry & Cytochemistry, Apr. 1, 2001, pp. 483-490, vol. 49, No. 4.
Stridsberg, M. et al., "Measurements of Chromogranin A, Chromogranin B (Secretogranin I), Chromogranin C (Secretogranin II) and Pancreastatin in Plasma and Urine from Patients with Carcinoid Tumours and Endocrine Pancreatic Tumours", Journal of Endocrinology, Jan. 1, 1995, pp. 49-59, vol. 144, No. 1, Society for Endocrinology, United Kingdom.
Hancock, David C. et al., "Synthetic Peptides as Antigens for Antibody Production", Methods in Molecular Biology, 2005, pp. 13-26, vol. 295.
"Antigen Design and Administration", Max Planck Institute of Molecular Cell Biology and Genetics, pp. 1-4, [available at at hymanlab.mpi-cbg.de/hyman_lab/general/], date unavailable.

(Continued)

*Primary Examiner* — Kimberly Ballard
(74) *Attorney, Agent, or Firm* — McBee Moore & Vanik IP, LLC; Susan E. Shaw McBee (57) ABSTRACT

The present invention relates to an immunoassay method for the detection of Chromogranin A (or fragment(s) thereof) comprising the steps of contacting a sample suspected of comprising Chromogranin A with a first antibody or an antigen-binding fragment or derivative thereof specific for Chromogranin A and a second antibody or an antigen-binding fragment or derivative thereof specific for Chromogranin A under conditions allowing for the formation of a ternary complex between Chromogranin A and the two antibodies or antigen-binding fragments or derivates thereof, and detecting the binding of the two antibodies or antigen-binding fragments or derivates thereof to Chromogranin A. Also provided are antibodies directed against amino acid residues 124 to 144 and 280 to 301 of Chromogranin A and their use in the immunoassay method.

8 Claims, 2 Drawing Sheets

Specification includes a Sequence Listing.

(56) References Cited

OTHER PUBLICATIONS

Deftos, Leonard J. et al., "Granins and Prostate Cancer", Urology, May 1998, pp. 141-145, 51 (Supplement 5A).
Ramage, John K. et al., "Guidelines for the management of gastroenteropancreatic neuroendocrine (including carcinoid) tumours (NETs)", Gut, 2012, pp. 6-32, vol. 61.
Vinik, Aaron I. et al., "Biochemical Testing for Neuroendocrine Tumors", Pancreas, Nov. 2009, pp. 876-889 vol. 38, No. 8.
Jensen, Eric H. et al., "Biomarkers Predict Outcomes Following Cytoreductive Surgery for Hepatic Metastases from Functional Carcinoid Tumors", Annals of Surgical Oncology, 2007, pp. 780-785, vol. 14, No. 2.
Goetze, Jens P. et al., "Chromogranin A as a biomarker in cardiovascular disease", Biomarkers Med., 2014, pp. 133-140, vol. 8, No. 1.
Soell, Martine et al., "Chromogranin A Detection in Saliva of Type 2 Diabetes Patients", Bosn J. Basic Med Sci, Feb. 2010, pp. 2-8, vol. 10, No. 1.
Peracchi, M. et al., "Plasma chromogranin A in patients with autoimmune chronic atrophic gastritis, enterochromaffin-like cell lesions and gastric carcinoids", European Journal of Endocrinology, 2005, pp. 443-448, vol. 152.
Kleveland, Ola et al., "Hypergastrinemia as a Cauuse of Chromogranin A Increase in Blood in Patients Suspected to Have Neuroendocrine Tumor", Digestion, 2001, pp. 71-74, vol. 64.
Sorhaug, Sveinung et al., "Increased serum levels of chromogranin A in male smokers with airway obstruction", ERJ Express, May 17, 2006.
Lloyd et al., "Modelling the human immune response: performance of a 10e11 human antibody repertoire against a broad panel of therapeutically relevant antigens", Protein Engineering, Design and Selection, Mar. 1, 2009, pp. 159-168, vol. 22, No. 3, https://doi.org/10.1093/protein/gzn058.
Brown et al., "Tolerance of single, but not multiple, amino acid replacements in antibody VH CDR 2: a means of minimizing B cell wastage from somatic hypermutation?", Journal of Immunology, May 1996, pp. 3259-3291, vol. 156, No. 9.
Vajdos et al., "Comprehensive functional maps of the antigen-binding site of an anti-ErbB2 antibody obtained with shotgun scanning mutagenesis", Journal of Molecular Biology, Jul. 5, 2002, pp. 415-428, vol. 320, No. 2, DOI: 10.1016/S0022-2836(02)00264-4.
Popovici et al., "Automated two-site immunofluorescent assay for the measurement of serum chromogranin A", Clinical Biochemistry, 2014, pp. 87-91, vol. 47, http://dx.doi.org/10.1016/j.clinbiochem.2013.10.029, Available online Nov. 5, 2013.
Harlow, E. and Lane, D., "Antibodies: A Laboratory Manual", 1988, pp. 553, 555-561, 578-582, and 591-592, Cold Spring Harbor Laboratory Press, Cold Spring Harbor, NY.
Mathis et al., "Probing Molecular Interactions with Homogeneous Techniques Based on Rare Earth Cryptates and Fluorescence Energy Transfer", Clinical Chemistry, 1995, pp. 1391-1397, vol. 41, No. 9.
Wolf et al., "Comparison of the Automated KRYPTOR Chromogranin A Assay with the DAKO ELISA", Clinical Laboratory, 2014, pp. 2103-2106, vol. 60.
Banks, P., "The Release of Protein from the Stimulated Adrenal Medulla," Biochem. J., (1965), vol. 97: pp. 40c-41c.
Corti, Angela, et al., "Antigenic regions of human chromogranin A and their topographic relationships with structural/functional domains," Eur. J. Biochem., (1996), vol. 235: pp. 275-280.
Corti, Angela, et al., "Characterisation of circulating chromogranin A in human cancer patients," British Journal of Cancer, (1996), vol. 73: pp. 924-932.
Curry, W.J., et al., "Isolation and primary structure of a novel chromogranin A-derived peptide, WE-14, from a human midgut carcinoid tumour," Federation of European Biochemical Societies, (1992), vol. 301, No. 3: pp. 319-321.

Galindo, Estelle, et al., "Chromostatin, a 20-amino acid peptide derived from chromogranin A, Inhibits chromaffic cell secretion," Proc. Natl. Acad. Sci. USA, (1991), vol. 88: pp. 1426-1430.
Kim, Taeyoon, et al., "Chromogranin A, an "On/Off" Switch Controlling Dense-Core Secretory Granule Biogenesis," Cell, (2001), vol. 106: pp. 499-509.
Kirchmair, Rudolf, et al., "Large variations in the proteolytic formation of a chromogranin A-derived peptide (GE-25) in neuroendocrine tissues," Biochem. J., (1995), vol. 310: pp. 331-336.
Mahata, S.K., et al., "Novel autocrine feedback control of catecholamine release. A discrete chromogranin a fragment is a noncompetitive nicotinic cholinergic antagonist.," Journal of Clinical Investigation, (1997), vol. 100, No. 6: 1623-1633.
Metz-Boutigue, Marie-Helene, et al., "Intracellular and extracellular processing of chromogranin A Determination of cleavage sites," Eur. J. Biochem. (1993), vol. 217: pp. 247-257.
Stridsberg, M., et al., "A comparison between three commercial kits for chromogranin A measurements," Journal of Endocrinology, (2003), vol. 177: pp. 337-341.
Strub, Jean-Marc, et al, "Phosphorylation and O-Glycosylation Sites of Bovine Chromogranin A from Adrenal Medullary Chromaffin Granules and Their Relationship with Biological Activities," Journal of Biological Chemistry, (1997), vol. 272, No. 18: pp. 11928-11936.
Taupenot, Laurent, et al, "The Chromogranin-Secretogranin Family," New England Journal of Medicine, (2003), vol. 348: pp. 1134-1149.
Vinik, Aaron, et al., "NANETS Consensus Guidelines for the Diagnosis of Neuroendocrine Tumor," Pancreas, (2010), vol. 39, No. 6: pp. 713-734.
Deftos, L. J., "Chromogranin A: Its Role in Endocrine Function and as an Endocrine and Neuroendocrine Tumor Marker," Endocrine Reviews, (1991), vol. 12, No. 2: pp. 181-188.
Drees, Betty ., et al., "Bovine Parathyroid Glands Secrete a 26-kDa N-Terminal Fragment of Chromogranin-A which Inhibits Parathyroid Cell Secretion," Endocrinology, (1991), vol. 129, No. 6: pp. 3381-3387.
Fasciotto, Brigitte H., et al., "Parastatin (Porcine Chromogranin A347-419), a Novel Chromogranin A-Derived Peptide, Inhibits Parathyroid Cell Secretion," Endocrinology, (1993), vol. 133, No. 2: pp. 461-466.
Pape, Ulrich-Frank, et al., "ENETS Consensus Guidelines for the Management of Patients with Neuroendocrine Neoplasms from the Jejuno-Ileum and the Appendix Including Goblet Cell Carcinomas," Neuroendocrinology, (2012), vol. 95: pp. 135-156.
Tatemoto, Kazuhiko, et al., "Pancreastatin, a novel pancreatic peptide that inhibits insulin secretion," Nature, (1986), vol. 324: pp. 476-478.
Extended European Search Report of European Patent Application No. 19202912.2 dated Feb. 24, 2020.
Ferrero-Pous, M. et al., "Serum chromogranin-A in advanced prostate cancer", BJU International, 2001, pp. 790-796, No. 88.
Malaguarnera, Michele et al., "Elevated chromogranin A (CgA) serum levels in the patients with advanced pancreatic cancer", Archives of Gerontology and Geriatrics, 2009, pp. 213-217, vol. 48.
Sasaki, Tetsuro et al., "Changes in Chromogranin A Serum Levels During Endocrine Therapy in Metastatic Prostate Cancer Patients", European Urology, 2005, pp. 224-230, vol. 48.
Stridsberg, M., et al., "Fragments of chromogranin A are present in the urine of patients with carcinoid tumours development of a specific radioimmunoassay for chromogranin A and its fragments," Journal of Endocrinology, (1993), vol. 139, No. 2 : 329-NP.
Bernini et al. British Journal of Cancer (2001) 84(5): 636-642.
Borglum et al. Clinical Chemistry (2007) 53(3) 438-446.
Leon et al., "Comparison between two methods in the determination of circulating chromagranin A in neuroendocrine tumors (NETs): Results of a prospective multicenter observational study," International Journal of Biological Markers, Wichtig Editore, Milan, IT, vol. 20, No. 3, Jul. 1, 2005, pp. 156-168, XP008172090.
O'Dorsio et al., "Development of a Highly Sensitive and Specific Carboxy-Terminal Human Pancreastatin Assay to Monitor Neuroendocrine Tumor Behavior," Pancreas, Raven Press, New York, NY, US, vol. 39, No. 5, Jul. 1, 2010, pp. 611-616, XP008172097.

(56) References Cited

OTHER PUBLICATIONS

Dillen et al., "Enzyme-linked immunosorbent assay for chromogranin A," Clinical Chemistry 1989 US, vol. 35, No. 9, 1989, pp. 1934-1938, XP008172099.

Kimura et al., "Immunohistochemical localization of chromostatin and pancreastatin, chromogranin A-Derived bioactive peptides, in normal and neoplastic neuroendocrine tissues" Endocrine Pathology, Humana Press, US, vol. 6, No. 1, Feb. 1, 1995, pp. 35-43, XP008172084.

\* cited by examiner

SEQUENCE LISTING

```
<160> NUMBER OF SEQ ID NOS: 5

<210> SEQ ID NO 1
<211> LENGTH: 439
<212> TYPE: PRT
<213> ORGANISM: Homo sapiens
<220> FEATURE:
<221> NAME/KEY: MISC_FEATURE
<222> LOCATION: (1)..(439)
<223> OTHER INFORMATION: Human Chromogranin A without signal peptide

<400> SEQUENCE: 1

Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
                20                  25                  30

Pro Val Ser Gln Glu Cys Phe Glu Thr Leu Arg Gly Asp Glu Arg Ile
            35                  40                  45

Leu Ser Ile Leu Arg His Gln Asn Leu Leu Lys Glu Leu Gln Asp Leu
        50                  55                  60

Ala Leu Gln Gly Ala Lys Glu Arg Ala His Gln Gln Lys Lys His Ser
65                  70                  75                  80

Gly Phe Glu Asp Glu Leu Ser Glu Val Leu Glu Asn Gln Ser Ser Gln
                85                  90                  95

Ala Glu Leu Lys Glu Ala Val Glu Glu Pro Ser Ser Lys Asp Val Met
            100                 105                 110

Glu Lys Arg Glu Asp Ser Lys Glu Ala Glu Lys Ser Gly Glu Ala Thr
        115                 120                 125

Asp Gly Ala Arg Pro Gln Ala Leu Pro Glu Pro Met Gln Glu Ser Lys
130                 135                 140

Ala Glu Gly Asn Asn Gln Ala Pro Gly Glu Glu Glu Glu Glu Glu Glu
145                 150                 155                 160

Glu Ala Thr Asn Thr His Pro Pro Ala Ser Leu Pro Ser Gln Lys Tyr
                165                 170                 175

Pro Gly Pro Gln Ala Glu Gly Asp Ser Glu Gly Leu Ser Gln Gly Leu
            180                 185                 190

Val Asp Arg Glu Lys Gly Leu Ser Ala Glu Pro Gly Trp Gln Ala Lys
        195                 200                 205

Arg Glu Glu Glu Glu Glu Glu Glu Glu Ala Glu Ala Gly Glu Glu
210                 215                 220
```

```
Ala Val Pro Glu Glu Glu Gly Pro Thr Val Val Leu Asn Pro His Pro
225                 230                 235                 240

Ser Leu Gly Tyr Lys Glu Ile Arg Lys Gly Glu Ser Arg Ser Glu Ala
                245                 250                 255

Leu Ala Val Asp Gly Ala Gly Lys Pro Gly Ala Glu Glu Ala Gln Asp
            260                 265                 270

Pro Glu Gly Lys Gly Glu Gln Glu His Ser Gln Gln Lys Glu Glu Glu
        275                 280                 285

Glu Glu Met Ala Val Val Pro Gln Gly Leu Phe Arg Gly Gly Lys Ser
    290                 295                 300

Gly Glu Leu Glu Gln Glu Glu Arg Leu Ser Lys Glu Trp Glu Asp
305                 310                 315                 320

Ser Lys Arg Trp Ser Lys Met Asp Gln Leu Ala Lys Glu Leu Thr Ala
                325                 330                 335

Glu Lys Arg Leu Glu Gly Gln Glu Glu Glu Asp Asn Arg Asp Ser
            340                 345                 350

Ser Met Lys Leu Ser Phe Arg Ala Arg Ala Tyr Gly Phe Arg Gly Pro
        355                 360                 365

Gly Pro Gln Leu Arg Arg Gly Trp Arg Pro Ser Ser Arg Glu Asp Ser
    370                 375                 380

Leu Glu Ala Gly Leu Pro Leu Gln Val Arg Gly Tyr Pro Glu Glu Lys
385                 390                 395                 400

Lys Glu Glu Gly Ser Ala Asn Arg Arg Pro Glu Asp Gln Glu Leu
                405                 410                 415

Glu Ser Leu Ser Ala Ile Glu Ala Glu Leu Glu Lys Val Ala His Gln
            420                 425                 430

Leu Gln Ala Leu Arg Arg Gly
        435

<210> SEQ ID NO 2
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: residues 124-144 of human Chromogranin A

<400> SEQUENCE: 2

Ser Gly Glu Ala Thr Asp Gly Ala Arg Pro Gln Ala Leu Pro Glu Pro
1               5                   10                  15

Met Gln Glu Ser Lys
            20

<210> SEQ ID NO 3
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: residues 280-301 of human Chromogranin A

<400> SEQUENCE: 3

Glu His Ser Gln Gln Lys Glu Glu Glu Glu Met Ala Val Val Pro
1               5                   10                  15

Gln Gly Leu Phe Arg Gly
            20
```

```
<210> SEQ ID NO 4
<211> LENGTH: 22
<212> TYPE: PRT
<213> ORGANISM: Artificial Sequence
<220> FEATURE:
<223> OTHER INFORMATION: Antigenic peptide fragment of human
      Chromogranin A

<400> SEQUENCE: 4

Cys Ser Gly Glu Ala Thr Asp Gly Ala Arg Pro Gln Ala Leu Pro Glu
1               5                  10                  15

Pro Met Gln Glu Ser Lys
            20

<210> SEQ ID NO 5
<211> LENGTH: 23
<212> TYPE: PRT
<213> ORGANISM: Artificial Sequence
<220> FEATURE:
<223> OTHER INFORMATION: Antigenic peptide fragment of human
      Chromogranin A

<400> SEQUENCE: 5

Cys Glu His Ser Gln Gln Lys Glu Glu Glu Glu Met Ala Val Val
1               5                  10                  15

Pro Gln Gly Leu Phe Arg Gly
            20
```

IMMUNOASSAY AND ANTIBODIES FOR THE DETECTION OF CHROMOGRANIN A

CROSS-REFERENCE TO RELATED APPLICATIONS

This application is a continuation of U.S. patent application Ser. No. 15/303,521, filed 11 Oct. 2016, which is a National Stage entry of International Application No. PCT/EP2015/058045, filed 14 Apr. 2015, which claims priority to European Patent Application No. 14164809.7, filed 15 Apr. 2014. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2905193-019001_ST25.txt" created on 12 Mar. 2020, and 5,666 bytes in size) is submitted concurrently with the instant application, and the entire contents of the Sequence Listing are incorporated herein by reference.

BACKGROUND OF THE INVENTION

Chromogranin A (CgA) is a protein that was identified and isolated in 1965 from chromaffin cells of bovine adrenal medulla (Banks et al. 1965. *Biochem J* 97 : 40C-1C; Taupenot et al. 2010. *New Eng J Med.* 348: 1134-49). Chromaffin cells are neuroendocrine cells found mostly in the medulla of the adrenal glands in mammals Chromogranin A is an established tumor marker in a variety of neuroendocrine tumors, a heterogeneous group of rare neoplasms from neurendocrine cells comprising multiple endocrine neoplasia, type 1 and type 2 (MEN1/MEN2), medullary thyroid carcinoma, carcinoid tumors, islet cell tumors, pheochromocytoma/paraganglioma, poorly differentiated/small cell/atypical lung carcinoid, small cell carcinoma of the lung, Merkel cell carcinoma (Deftos et al. 1991. *Endocr. Rev.* 12:181-7; Corti et al. 1996. *Br J Cancer* 73:924-32) and mentioned in several guidelines (Ramage et al. 2012. *Gut* 61:6-32; Vinik et al. 2010. *NANETS Pancreas* 39(6): 713-734; Pape et al. 2012. *ENETS* 95: 135-156).

Human Chromogranin A has a sequence of 439 amino acid residues (see SEQ ID NO:1) constituting a 49 kDa acidic glycoprotein that is stored and released from the chromaffin granules of endocrine cells, neurons and neurendocrines cells along with their respective hormones, neurotransmitters, and neuropeptides (Kim et al. 2001. *Cell* 106: 499-509).

Chromogranin A is the main member of the chromogranin/secretogranin family which consists of a group of proteins derived from different genes but share a number of characteristics, namely an abundance of acidic amino acid residues and numerous pairs of basic amino acids as potential positions for post-translational processing (Metz-Boutigue et al. 1993. *Eur. J. Biochem* 217: 247-257) and cleavage.

CgA is the precursor of several biologically active peptide fragments that have been described in human and in other species: vasostatins (Drees et al. 1991. *Endocrinology* 129: 3381-7), chromostatin (Galindo et al. 1991. *Proc Natl Acad Sci USA* 88: 1426-30), chromacins (Strub et al. 1997. *J Biol Chem* 272: 11928-36), pancreastatin (Tatemoto et al. 1986. *Nature* 324: 476-8), WE-14 (Curry et al. 1992. *FEBS Lett* 301: 319-321), catestatin (Mahata et al. 1997. *J Clin Invest* 100: 1623-33), parastatin (Fasciotto et al. 1993. *Endocrinology* 133: 461-6) and GE-25 (Kirchmair et al. 1995. *Biochem J* 310 (Pt 1): 331-6). In the UniProt database, additional peptides for human Chromogranin A (accession number: P 10645) are mentioned, based on the cleavage sites that can predict the peptides to be released: vasostatin-1 comprises amino acid sequence 1-76, vasostatin-2 comprises amino acid sequence 1-113, EA-92 comprises amino acid sequence 116-207, ES-43 comprises amino acid sequence 210-242, pancreastatin comprises amino acid sequence 254-301, SS-18 comprises amino acid sequence 304-321, WE-14 comprises amino acid sequence 324-337, WA-8 comprises amino acid sequence 324-331, LF-19 comprises amino acid sequence 340-358, AL-11 comprises amino acid sequence 362-372, GV-19 comprises amino acid sequence 375-393, GR-44 comprises amino acid sequence 395-438 and ER-37 comprises amino acid sequence 402-438. Moreover, it has been shown that different neurendocrine cells can process the molecule differently (Portela-Gomes et al. 2001. *J Histochem Cytochem* 4: 483-90).

Chromgranin A has been described as a biomarker for a number of diseases and conditions including cancer, for example prostate cancer (WO 2013/070088 A1; WO 2013/070089 A1; U.S. Pat. No. 6,238,877 B1 ; WO 2012/065025 A2).

Today, four non radiative CE-marked commercial assays for the detection of Chromogranin A are available: The Cis-Bio ELISA assay (Cisbio Bioassays, Codolet, France) uses two monoclonal antibodies directed against epitopes corresponding to amino acids 145-197 and 219-234, the DAKO ELISA assay (Dako Denmark A/S, Glostrup, Denmark) uses rabbit polyclonal antibodies directed against a 23 kDa C-terminal fragment, the Euro-Diagnostica NEOLISA™ sandwich ELISA assay (Euro Diagnostica AB, Malmö, Sweden) uses two monoclonal antibodies directed against epitopes corresponding to amino acids 236-251 and 264-279 (also see WO 2011/135035 A1 and WO 99/58980 A1).

The only available fully automated assay for the detection of Chromogranin A is the Chromogranin A KRYPTOR assay (Thermo Fisher Scientific B.R.A.H.M.S GmbH, Hennigsdorf, Germany) which uses two monoclonal antibodies, one monoclonal antibody binding to an epitope corresponding to amino acids 250-301 (Popovici et al. 2014. *Clin Biochem* 47: 87-91).

Due to high proteolysis of the molecule, the measured concentration in these assays can vary depending on the storage of the collected sample over the time and depending on the fragment being measured by the antibodies in the assay, thus an improved assay for Chromogranin A should address the most stable fragments of the molecule and be assessed in terms of sample stability under different storage conditions.

Different publications describe the impact of antibody epitopes and assay design on clinical performance of Chromogranin A immunoassays (Corti et al. 1996. *Eur. J. Biochem* 235: 275-280 Stridsberg et al. 2003. *J Endocrinol* 177: 337-41).

SUMMARY OF THE INVENTION

The present invention relates to a new assay design for the detection of Chromogranin A or fragments thereof. This assay uses one or more antibodies that bind to epitopes, which were previously characterized as poor or non-binding antigenic sites (Corti et al. 1996. *Eur J. Biochem* 235: 275-280). The assay of the present invention surprisingly shows an improved analyte stability in the sample compared to the existing fully automated Chromogranin A KRYPTOR assay (B.R.A.H.M.S GmbH, Hennigsdorf, Germany). The immunoassay provided herein further has a broad detection range, i.e. detection of the target protein is possible at least in a concentration range from about 9 ng/ml to about 3 mg/ml. The broad detection range leads to an economic advantage, because less samples need to be diluted.

Hence, the assay of the present invention can, e.g., be used as a research tool and in clinical applications for the detection of Chromogranin A over a wide range of concentrations and with a high specificity. In terms of clinical applications, the assay of the present invention can be used for the detection of Chromogranin A in patients samples for diagnosis, prognosis, risk assessment, risk stratification, therapy-control and/or post-operative control of a disorder or medical condition.

In particular, the present invention provides an immunoassay method for the detection of Chromogranin A or a fragment thereof comprising the steps of:

a) contacting a sample suspected of comprising Chromogranin A with a first antibody or an antigen-binding fragment or derivative thereof specific for Chromogranin A and a second antibody or an antigen-binding fragment or derivative thereof specific for Chromogranin A under conditions allowing for the formation of a ternary complex between Chromogranin A and the two antibodies or antigen-binding fragments or derivates thereof, and b) detecting the binding of the two antibodies or antigen-binding fragments or derivates thereof to Chromogranin A.

In the immunoassay method according to the invention said first antibody may be specific for an epitope in the sequence of Chromogranin A (SEQ ID NO:1), preferably in the sequence spanning amino acids 124-144 of SEQ ID NO:1.

The immunoassay method of the invention can be used in the context of diagnostic methods. The invention further relates to antibodies and kits for the use in the methods of the invention.

DETAILED DESCRIPTION OF THE INVENTION

Information Relating to Deposit of Biological Material, in Compliance with the Requirements of M.P.E.P. § 2411 & 37 C.F.R. § 1.809

The following is a specific reference to a first biological deposit, in compliance with the requirements of M.P.E.P. § 2411 and 37 C.F.R. § 1.809 for antibody produced by hybridoma cell line 537/H2:

(1) The accession number for the deposit: DSM ACC3231;

(2) The date of the deposit: 20 Feb. 2014;

(3) A description of the deposited biological material sufficient to specifically identify it and to permit examination: antibody produced by the hybridoma cell line 537/H2 deposited at the Leibniz-Institut DSMZ-Deutsche Sammlung von Mikroorganismen und Zellkulturen GmbH (DSMZ), Inhoffenstraβe 7B, 38124 Braunschweig, Germany, on Feb. 20, 2014 as DSM ACC3231; and (4) The name and address of the depository: Leibniz-Institut DSMZ-Deutsche Sammlung von Mikroorganismen und Zellkulturen GmbH (DSMZ), Inhoffenstraβe 7B, 38124 Braunschweig, Germany.

The following is a specific reference to a second biological deposit, in compliance with the requirements of M.P.E.P. § 2411 and 37 C.F.R. § 1.809 for antibody produced by the hybridoma cell line 541/E2:

(1) The accession number for the deposit: DSM ACC323s;

(2) The date of the deposit: 20 Feb. 2014;

(3) A description of the deposited biological material sufficient to specifically identify it and to permit examination: antibody produced by the hybridoma cell line 541/E2 deposited at the Leibniz-Institut DSMZ-Deutsche Sammlung von Mikroorganismen und Zellkulturen GmbH (DSMZ), Inhoffenstraβe 7B, 38124 Braunschweig, Germany, on Feb. 20, 2014 as DSM ACC3232; and (4) The name and address of the depository: Leibniz-Institut DSMZ-Deutsche Sammlung von Mikroorganismen und Zellkulturen GmbH (DSMZ), Inhoffenstraβe 7B, 38124 Braunschweig, Germany.

The present invention relates to an immunoassay method for the detection of Chromogranin A or fragments thereof. The immunoassay method is based on the detection of Chromogranin A using one or more antibodies, preferably monoclonal antibodies, that are specific for Chromogranin A. Preferably, the immunoassay detects epitopes in the sequence spanning amino acid residues 124 to 144 and/or 280 to 301 of the Chromogranin A sequence according to SEQ ID NO:1. Hence, fragments of Chromogranin A encompassing amino acid residues 124 to 144 and/or 280 to 301 of the Chromogranin A sequence can also be detected with the immunoassay provided herein. Herein, the terms "Chromogranin A or a fragment thereof" or "Chromogranin or fragment(s) thereof" therefore encompass Chromogranin A and all fragments thereof that comprise the epitope(s) detected by the immunoassay of the invention, i.e. that can be detected using the immunoassay of the invention. Preferably, the assay employs at least one antibody that detects an epitope in the sequence spanning amino acid residues 124 to 144 of the Chromogranin A sequence according to SEQ ID NO:1. Chromogranin A or—as the case may be—fragment(s) thereof can according to the immunoassay of the invention be qualitatively and/or quantitatively detected by the binding of one or preferably two antibodies to Chromogranin A or a fragment thereof. In the case of a sandwich immunoassay (i.e. employing two antibodies) the presence of Chromogranin A or its fragment will be detected if both antibodies bind the Chromogranin A or its fragment. In other words the invention in one embodiment relates to an immunoassay for the detection of Chromogranin A or a fragment thereof in a sample comprising the steps of contacting said sample with a first anti-Chromogranin A antibody (or an antigen-binding fragment or derivative thereof) and a second anti-Chromogranin A antibody (or an antigen-binding fragment or derivative thereof) and detecting the presence of ternary immune complexes of said antibodies and Chromogranin A (or fragment(s) thereof). The immune complexes will form under conditions that allow an immunoreaction between said antibody/antibodies and said sample (i.e. under conditions allowing for the binding of the antibody/antibodies to Chromogranin A or fragment(s) thereof, i.e. the formation of a ternary complex in case of a sandwich assay). In the immunoassay, preferably a combination of two antibodies may be used, e.g. in a sandwich format (see below). Hence, the present invention pertains to an immunoassay method for the detection of Chromogranin A (or a fragment thereof) comprising the steps of a) contacting a sample suspected of comprising Chromogranin A (or a fragment thereof) with a first antibody or an antigen-binding fragment or derivative thereof specific for Chromogranin A or a fragment thereof and a second antibody or an antigen-binding fragment or derivative thereof specific for Chromogranin A or a fragment thereof, and b) detecting the binding of the two antibodies or antigen-binding fragments or derivates thereof to Chromogranin A or a fragment thereof. In the immunoassay method according to the invention said first antibody is preferably specific for an epitope in the sequence of Chromogranin A (SEQ ID NO:1), preferably in the sequence spanning amino acids 124 to 144 of SEQ ID NO:1. The first antibody is preferably a monoclonal antibody.

The present invention also pertains to an immunoassay method for the detection of Chromogranin A (or a fragment thereof) comprising the steps of a) contacting a sample suspected of comprising Chromogranin A (or a fragment thereof) with a first antibody or an antigen-binding fragment or derivative thereof specific for Chromogranin A or a fragment thereof and a second antibody or an antigen-binding fragment or derivative thereof specific for Chromogranin A or a fragment thereof under conditions allowing for the formation of a ternary complex between Chromogranin A or a fragment thereof and the two antibodies or antigen-binding fragments or derivates thereof, and b) detecting the binding of the two antibodies or antigen-binding fragments or derivates thereof to Chromogranin A or a fragment thereof. In the immunoassay method according to the invention said first antibody is preferably specific for an epitope in the sequence of Chromogranin A (SEQ ID NO:1), preferably in the sequence spanning amino acids 124 to 144 of SEQ ID NO:1. The first antibody is preferably a monoclonal antibody.

The invention also relates to an immunoassay method for the detection of Chromogranin A or fragments thereof comprising the steps of a) contacting a sample suspected of comprising Chromogranin A with an antibody or an antigen-binding fragment or derivative thereof specific for Chromogranin A or a fragment thereof under conditions allowing for the formation of an immune complex between Chromogranin A and the antibody or antigen-binding fragments or derivates thereof, wherein said first antibody is specific for an epitope spanning amino acids 124 to 144 of the Chromogranin A sequence (SEQ ID NO:1). The antibody being specific for the epitope spanning amino acids 124 to 144 of the Chromogranin A sequence is preferably the antibody produced by hybridoma cell line 537/H2 deposited at the Leibniz-Institut DSMZ-Deutsche Sammlung von Mikroorganismen und Zellkulturen GmbH (DSMZ), Inhoffenstraβe 7B, 38124 Braunschweig, Germany, on Feb. 20, 2014 as DSM ACC3231.

In the following the term "antibody" also comprises antigen-binding fragments or derivatives unless otherwise stated.

The term "antibody" generally comprises monoclonal and polyclonal antibodies and binding fragments thereof, in particular Fc-fragments as well as so called "single-chain-antibodies" (Bird R. E. et al (1988) *Science* 242:423-6), *chimeric, humanized, in particular CDR-grafted antibodies, and dia or tetrabodies* (Holliger P. et al (1993) *Proc. Natl. Acad. Sci. U.S.A.* 90:6444-8). Also comprised are immunoglobulin-like proteins that are selected through techniques including, for example, phage display to specifically bind to the molecule of interest contained in a sample. In this context the terms "specific" and "specific binding" refer to antibodies raised against the molecule of interest or a fragment thereof. An antibody is considered to be specific, if its affinity towards the molecule of interest (here: Chromogranin A) or the aforementioned fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. As stated herein above, monoclonal antibodies are preferred.

As will be discussed herein below in more detail the (first and/or second) antibodies or antigen-binding fragments or derivatives thereof of the immunoassay method as described herein may for instance be polyclonal antibodies, monoclonal antibodies or genetically engineered monoclonal antibodies.

In the immunoassay method according to the invention said first antibody may be specific for an epitope in the sequence of Chromogranin A (SEQ ID NO:1), preferably in the sequence spanning amino acids 124 to 144 of SEQ ID NO:1. The first antibody is preferably a monoclonal antibody.

In the immunoassay method according to the invention said second antibody may be specific for an epitope in the sequence of Chromogranin A (SEQ ID NO:1), preferably in the sequence spanning amino acids 280 to 301 of SEQ ID NO:1. The second antibody is preferably a monoclonal antibody.

In a particular embodiment of the immunoassay of the invention, the first antibody is specific for an epitope in the sequence of Chromogranin A (SEQ ID NO:1) spanning amino acid residues 124-144 and the second antibody is specific for an epitope in the sequence of Chromogranin A (SEQ ID NO:1) spanning amino acid residues 280 to 301. The first and second antibodies are preferably monoclonal antibodies.

The first antibody or antigen-binding fragment or derivative thereof may for example be produced by the hybridoma cell line 537/H2 deposited at the DSMZ (Inhoffenstraβe 7B, 38124 Braunschweig, Germany) on Feb. 20, 2014 as DSM ACC3231. The antibody produced by hybridoma cell line 537/H2 binds specifically to amino acid residues 124 to 144 of the Chromogranin A sequence (SEQ ID NO:1), i.e. to SEQ ID NO:2. It has been raised against the antigenic peptide of SEQ ID NO:4.

The second antibody or antigen-binding fragment or derivative thereof may for example be produced by the hybridoma cell line 541/E2 deposited at the DSMZ, Inhoffenstraβe 7B, 38124 Braunschweig, Germany, on Feb. 20, 2014 as DSM ACC3232. The antibody produced by hybridoma cell line 541/E2 binds specifically to amino acid residues 280 to 301 of the Chromogranin A sequence (SEQ ID NO:1), i.e. to SEQ ID NO:3. It has been raised against the antigenic peptide of SEQ ID NO:5.

In a particular embodiment of the immunoassay method of the invention, the first antibody is produced by the hybridoma cell line 537/H2 deposited at the DSMZ, Inhoffenstraβe 7B, 38124 Braunschweig, Germany, on Feb. 20, 2014 as DSM ACC3231 and the second antibody is produced by the hybridoma cell line 541/E2 deposited at the DSMZ, Inhoffenstraβe 7B, 38124 Braunschweig, Germany, on Feb. 20, 2014 as DSM ACC3232.

The binding of the antibodies to Chromogranin A (or a fragment thereof) takes place under suitable conditions (i.e. allowing for immunoreactions, i.e. binding of the antibodies to Chromogranin A and formation of immune complexes). Such conditions are known to the skilled person and standard formats of immunoassays e.g. as described below can be used. Such conditions will preferably be under physiologic temperature, pH and ionic strength and can take place in media such as, for example, phosphate buffered saline (PBS).

The preferred detection methods comprise immunoassays in various formats such as for instance radioimmunoassay (RIA), chemiluminescence- and fluorescence-immunoassays, enzyme immunoassay (EIA), Enzyme-linked immunoassays (ELISA), Luminex-based bead arrays, protein microarray assays, rapid test formats such as for instance immunochromatographic strip tests, and Selected/Multiple reaction monitoring (SRM/MRM).

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety or vice versa. The amount of labeled antibody bound to the analyte is then measured by an appropriate method. The general composition and procedures involved with "sandwich assays" are well-established and known to the skilled person (*The Immunoassay Handbook, Ed.* David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference).

In a particularly preferred embodiment, the assay comprises two antibodies which are both present as dispersions in a liquid reaction mixture, wherein a first labelling component is attached to the first antibody, wherein said first labelling component is part of a labelling system based on fluorescence- or chemiluminescence-quenching or amplification, and a second labelling component of said marking system is attached to the second antibody, so that upon binding of both capture molecules to the analyte a measurable signal is generated that allows for the detection of the formed sandwich complexes in the solution comprising the sample.

Even more preferred, said labelling system may comprise rare earth cryptates or rare earth chelates in combination with fluorescence dye or chemiluminescence dye, in particular a dye of the cyanine type.

In the context of the present invention, fluorescence based assays may comprise the use of dyes, which may for instance be selected from the group comprising FAM (5-or 6-carboxyfluorescein), VIC, NED, Fluorescein, Fluorescein-isothiocyanate (FITC), IRD-700/800, Cyanine dyes, such as CY3, CYS, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarins such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, *Encyclopedia of chemical technology*, $4^{th}$ ed., executive editor, J. I. Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters. Chromogranin A may for example be detected using fully automated sandwich immunoassay systems on the B.R.A.H.M.S KRYPTOR compact PLUS instrument (Thermo Scientific B.R.A.H.M.S GmbH, Hennigsdorf/Berlin, Germany). This random access analyzer employs the sensitive Time Resolved Amplified Cryptate Emmission (TRACE) technology, based on a non-radioactive-transfer between two fluorophores.

In specific embodiments of the invention one of the antibodies (e.g. the first antibody) is labeled and the other antibody (e.g. the second antibody) is bound to a solid phase or can be bound selectively to a solid phase. However, as mentioned above, it is preferred in the context of methods of the invention that the first and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to Chromogranin A (or fragment(s) thereof), a measurable signal which permits detection of the resulting sandwich complexes in the measuring solution is generated.

As mentioned herein, an "assay" or "diagnostic assay" can be of any type applied in the field of diagnostics. Such an assay may be based on the binding of an analyte to be detected to one or more capture probes with a certain affinity. Concerning the interaction between antibodies and target molecules or molecules of interest, the affinity constant is preferably greater than $10^8$ M$^{-1}$.

The immunoassay method of the present invention may be used in the context of diagnostic and/or prognostic methods in which the presence and/or absence or the level of Chromogranin A (or fragment(s) thereof) is detected in a sample from a subject to be diagnosed. Chromogranin A has been implicated with a number of diseases and conditions including carcinoid tumors, neuroendrocrine tumors, prostate cancer, bladder cancer, gastritis, pulmonary disease, myocardial infarction, hypertension, heart failure, pulmonary diseases, thrombolysis, obesity and diabetes. Hence, the immunoassay of the present invention may be used in the diagnosis of a disease or condition selected from the group of cancer (including carcinoid tumors, neuroendocrine tumors, prostate cancer and bladder cancer), gastritis, pulmonary disease, myocardial infarction, hypertension, heart failure, pulmonary diseases, thrombolysis, obesity and diabetes.

The "sensitivity" of an assay relates to the proportion of actual positives which are correctly identified as such, i.e.

the ability to identify positive results (true positives positive results/number of positives). Hence, the lower the concentrations of the analyte that can be detected with an assay, the more sensitive is the assay. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having a prenatal discorder or condition) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disorder or condition ("diseased group"). In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

The invention further relates to a kit for the detection of Chromogranin A comprising
 (i) a first antibody or antigen-binding fragment or derivative thereof which is specific for Chromogranin A or a fragment thereof; and
 (ii) a second antibody or antigen-binding fragment or derivative thereof which is specific for Chromogranin A or a fragment thereof.

The first and second antibodies of the kit are preferably specific for the same Chromogranin A fragment or fragments.

For example, (i) the first antibody or antigen-binding fragment or derivative thereof is specific for an epitope comprised within the sequence of SEQ ID NO:1; and/or (ii) the second antibody or antigen-binding fragment or derivative thereof is specific for an epitope comprised within the sequence of SEQ ID NO:1. Preferably, the first antibody of the kit is a monoclonal anti-Chromogranin A antibody produced by hybridoma cell line 537/H2 deposited as DSM ACC3231 and/or the second antibody is a monoclonal anti-Chromogranin A antibody produced by hybridoma cell line 541/E2 deposited as DSM ACC3232.

The present invention also provides a hybridoma cell line selected from cell line 537/H2 deposited as DSM ACC3231 and cell line 541/E2 deposited as DSM ACC3232.

The invention e.g. further relates to the use of a kit according to the present invention in a sandwich immunoassay format for the detection and/or quantification of Chromogranin A or a fragment thereof in a biological sample from a bodily fluid. Such a fragment in one embodiment at least comprises a sequence spanning the two epitopes against which the two antibodies are directed, e.g. the kit can be used for the detection and/or quantification of Chromogranin A.

The term "sample" is preferably a biological sample. "Sample" as used herein may, e.g., refer to a sample of bodily fluid or tissue obtained for the purpose of diagnosis, prognosis, or evaluation of a subject of interest, such as a patient.

A "patient" or "subject" for the purposes of the present invention includes both humans and other animals, particularly mammals, and other organisms. Thus, the methods are applicable to both human diagnostics and veterinary applications. In a preferred embodiment the patient is a mammal, and in the most preferred embodiment the patient or subject is a human.

Preferably herein, the sample is a sample of a bodily fluid or a tissue of the subject. A bodily fluid sample is preferred. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, more preferably a serum sample or a plasma sample. Serum samples are the most preferred samples in the context of the present invention.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The method of the invention further relates to the determination of the level of Chromogranin A (or fragment(s) thereof) in a sample for diagnosis or prognosis or risk assessment or screening or therapy control or post-operative control for medical conditions.

The immunoassay, antibody or kit of the invention may therefore be used for the diagnosis, prognosis, risk assessment, risk stratification, therapy control and/or for post-operative control of a disorder or medical condition in a subject.

In the context of the present invention, the immunoassay, antibody or kit of the invention may therefore be used for therapy control and post-operative control of a disorder, wherein the disorder may be different types of cancer.

As mentioned herein above, in the context of the present invention, the disorder or medical condition in the subject may preferably be selected from cancer (including carcinoid tumors, neuroendocrine tumors, prostate cancer and bladder cancer), gastritis, pulmonary disease, myocardial infarction, hypertension, heart failure, pulmonary diseases, thrombolysis, obesity and diabetes.

In the context of the present invention, the disorder or medical condition in the subject is preferably selected from neuroendocrine tumours (NETs) including pheochromocytomas, pancreatic NETs, gastrointestinal NETs, neuroblastomas, medullary thyroid carcinomas, small cell lung cancer, multiple endocrine neoplasia 1 and multiple endocrine neoplasia 2 syndromes, prostate cancer, cardiovascular diseases, conditions related to infections and sepsis.

The term "biomarker" (biological marker) relates to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention. A biomarker may be measured on a biosample (as a blood, urine, or tissue test), it may be a recording obtained from a person (blood pressure, ECG, or Holter), or it may be an imaging test (Uteroplacental Doppler ultrasound, or nuchal translucency (Conde-Agudelo et al. 2004. *Obstet Gynecol* 104: 1367-1391; Bindra et al. 2002. *Ultrasound Obstet Gynecol* 20: 219-225)). Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule.

Herein "Chromogranin A" refers to human Chromogranin A. The amino acid sequence of human Chromogranin A is given in SEQ ID NO:1. The Chromogranin A polypeptides or derivatives according to the invention may also have posttranslational modifications such as glycolization, lip(o)idization, or derivatization.

"Diagnosis" in the context of the present invention relates to the recognition and (early) detection of a disease or clinical condition in a subject and may also comprise differential diagnosis. Also the assessment of the severity of a disease or clinical condition may in certain embodiments be encompassed by the term "diagnosis".

"Prognosis" relates to the prediction of an outcome or a specific risk for a subject suffering from a particular disease or clinical condition. This may include an estimation of the chance of recovery or the chance of an adverse outcome for said subject.

In the present invention, the term "risk assessment" or "risk stratification" relates to the grouping of subjects into different risk groups according to their further prognosis. Risk stratification also relates to stratification for applying preventive and/or therapeutic measures.

The term "therapy control" in the context of the present invention refers to the monitoring and/or adjustment of a therapeutic treatment of said patient.

The term "post-operative control" in the context of the present invention refers to the monitoring of said patient following a surgical procedure of said patient.

The term "screening" in the context of the present invention refers to a process of surveying a population, using a specific marker or markers and defined screening cut-off levels, to identify the individuals in the population at higher risk for a particular disorder. Screening is applicable to a population; diagnosis is applied at the individual patient level.

The following examples and figures are used for a more detailed explanation of the invention, but do not limit the invention to said examples and figures.

All patent and non-patent references cited herein are hereby incorporated by reference in their entirety.

SEQUENCES

```
Sequence 1 (SEQ ID NO: 1): Human Chromogranin A (CGA) without
signal peptide (UniProt Accession no. P10645); antigenic
epitopes are underlined:
1          11         21         31         41
LPVNSPMNKG DTEVMKCIVE VISDTLSKPS PMPVSQECFE TLRGDERILS 51         61         71         81         91
ILRHQNLLKE LQDLALQGAK ERAHQQKKHS GFEDELSEVL ENQSSQAELK 101        111        121        131        141
EAVEEPSSKD VMEKREDSKE AEKSGEATDG ARPQALPEPM QESKAEGNNQ 151        161        171        181        191
APGEEEEEEE EATNTHPPAS LPSQKYPGPQ AEGDSEGLSQ GLVDREKGLS 201        211        221        231        241
AEPGWQAKRE EEEEEEEEAE AGEEAVPEEE GPTVVLNPHP SLGYKEIRKG 251        261        271        281        291
ESRSEALAVD GAGKPGAEEA QDPEGKGEQE HSQQKEEEEE MAVVPQGLFR 301        311        321        331        341
GGKSGELEQE EERLSKEWED SKRWSKMDQL AKELTAEKRL EGQEEEEDNR 351        361        371        381        391
DSSMKLSFRA RAYGFRGPGP QLRRGWRPSS REDSLEAGLP LQVRGYPEEK 401        411        421        431
KEEEGSANRR PEDQELESLS AIEAELEKVA HQLQALRRG Sequence 2 (SEQ ID NO: 2): Epitope 1 of human Chromogranin
A (CGA) (corresponding to residues 124-144 of SEQ ID NO: 1):
1          11         21
SGEATDGARP QALPEPMQES K Sequence 3 (SEQ ID NO: 3): Epitope 2 of human Chromogranin A
(CGA) (corresponding to residues 280-301 of SEQ ID NO: 1):
1          11         21
EHSQQKEEEE EMAVVPQGLF RG Sequence 4 (SEQ ID NO: 4): Antigenic peptide fragment of
human Chromogranin A (CGA) (corresponding to residues
124-144 of SEQ ID NO: 1 plus additional cystein at
the N-terminal):
1          11         21
CSGEATDGAR PQALPEPMQE SK
```

-continued

Sequence 5 (SEQ ID NO: 5): Antigenic peptide fragment of
human Chromogranin A (CGA) (corresponding to residues
280-301 of SEQ ID NO: 1 plus additional cystein at the
N-terminal):
1          11         21
CEHSQQKEEE EEMAVVPQGL FRG

EXAMPLES

Example 1: Generation of Antibodies

Development of Monoclonal Antibodies

Immunogens were prepared as follows: CSGEATDGARPQALPEPMQESK (SEQ ID NO:4) peptide corresponding to the amino-acids region 124-144 of Chromogranin A molecule with an additional cystein at its N-terminal was covalently cross-linked with the carrier BSA. CEHSQQKEEEEEMAVVPQGLFRG (SEQ ID NO:5) peptide corresponding to the amino-acids region 280-301 of Chromogranin A molecule with an additional cystein at its N-terminal was covalently cross-linked with the carrier BSA.

Monoclonal antibodies against the Chromogranin A 124-144 and 280-301 peptides were generated by standard procedures (Harlow E, Lane D. *Antibodies—A Laboratory Manual*. Cold Spring Harbor: Cold Spring Harbor Laboratory, 1988; Lane 1985. *Journal of Immunology Methods* 81:223-228).

8-week-old female Balb/c mice were respectively immunized with by intra-peritoneal injections with 100 µg of 124-144 or 280-301 peptides diluted in complete Freund's adjuvant. Next injections were done using incomplete Freund's adjuvant at a 50 µg dose and at different time intervals during 61 days.

Prior fusion, the presence of the desired antibody was detected in the sera of the recipients using ELISA with 124-144 or 280-301 immobilized peptide. Then the clones 537/H2 and 541/E2 were screened by ELISA with immobilized rec. CGA (recombinant Chromogranin A was prepared by the French National of Scientific Research, "Plateforme de Production de Protéins Recombinantes" CRBM UMR 5237 CNRS, Montpellier).

For the isotype characterization, the Mouse Monoclonal Antibody Isotyping Kit (Roche) was used.

The antibodies were purified by protein A Fast Flow affinity chromatography (GE Healthcare Life Sciences) according to the manufacturer's instructions.

Labelling of Antibodies

In the final assay, the antibody 537/H2 was coupled to europium cryptate (CisBio Bioassays, Marcoule, France) and the antibody 541/E2 was coupled to Alexa Fluor 647® (Life Technologies, now part of Thermo Fisher Scientific). The coupling reactions were performed according to the manufacturer's protocols.

Example 2: Development of a Chromogranin A assay Using 124-144/280-301 Amino Acid Region Targeted Antibodies A homogenous sandwich fluoroimmunoassay using Time Resolved Amplified Cryptate Emission (TRACE) technology (Mathis, 1993. *Clin Chem* 39(9): 1953-9) was developed for the detection of a stable fragment of Chromogranin A.

The stock Cryptate-537/H2 conjugated antibody and Alexa Fluor®-541/E2 conjugate antibody were diluted at 0.265 µg/ml and 2.94 µg/ml with assay buffer (100 mM phosphate pH 7, 422 mM KF, 0.1% bovine serum albumin, 0.15 mg/ml mouse Ig and 0.07 mg/ml bovine Ig) respectively, prior to use.

The recombinant Chromogranin A was diluted in horse serum to give Chromogranin A standards. The immunoassay was performed by incubating 14 µl of sample/standard, 68 µl of Alexa Fluor®-541/E2 conjugate antibody solution and 68 µl of Cryptate-537/H2 conjugated antibody solution at 37° C. on B.R.A.H.M.S KRYPTOR instrument (Thermo Fisher Scientific B.R.A.H.M.S GmbH, Hennigsdorf/Berlin, Germany), according to the manufacturer's instructions. The reaction time of the assay was 29 min. The specific fluorescence (RFU) was measured by simultaneous dual wavelength measurement at 665 and 620 nm using a B.R.A.H.M.S KRYPTOR instrument. Direct reading range was defined up to 3000 ng/ml and functional assay sensitivity estimated to be of 13.1 ng/ml.

Example 3: Stability Following of Chromogranin A in Serum Samples Pools Using the CgA II Assay Three serum samples pools that had been frozen at ≤−16° C. just after collection were used for the study.

One pool was made from healthy individual serum samples (Pool 1) and the other two from pathological serum samples (pools 2 and 3).

Measurement time points were: after 1, 2 and 3 days at 2-8° C.; after 1, 2 and 3 days at 18-25° C.; after 1, 2 and 3 freeze/thaw cycles.

The measurements were done on a KRYPTOR instrument with the reagents and under conditions described above.

The criteria stated for considering stability of sample as acceptable is a loss ≤10% under the different conditions.

Results obtained (Table 1) show that the (537/H2-Cryptate; 541/E2-Alexa Fluor®) KRYPTOR assay is not sensitive to up to 3 freeze/thaw cycles, one day at 2-8° C. or at 18-25° C. The stability of the 2 pathological pools is better than the stability observed for the healthy-donors pool, as only a limited decrease of concentration is observed after 3 days at 2-8° C. or 18-25° C. (≤11%).

TABLE 1

Stability following of 3 serum samples pools using 537/H2-Cryptate; 541/E2-Alexa Fluor ® on KRYPTOR

|  | POOL 1 | | POOL 2 | | POOL 3 | |
| --- | --- | --- | --- | --- | --- | --- |
| Conditions | Conc. (ng/ml) | /Ref. | Conc. (ng/ml) | /Ref. | Conc. (ng/ml) | /Ref. |
| Reference | 85.5 | — | 880 | — | 2153 | — |
| 3 days 2-8° C. | 65.7 | −23% | 786 | −11% | 1981 | −8% |
| 2 days 2-8° C. | 62.9 | −26% | 797 | −9% | 2011 | −7% |
| 1 day 2-8° C. | 79.8 | −7% | 825 | −6% | 2098 | −3% |
| 3 days 18-25° C. | 69.9 | −18% | 789 | −10% | 1976 | −8% |
| 2 days 18-25° C. | 71.2 | −17% | 798 | −9% | 2047 | −5% |
| 1 days 18-25° C. | 78.5 | −8% | 816 | −7% | 2070 | −4% |

TABLE 1-continued

Stability following of 3 serum samples pools using 537/H2-Cryptate; 541/E2-Alexa Fluor ® on KRYPTOR

| Conditions | POOL 1 | | POOL 2 | | POOL 3 | |
|---|---|---|---|---|---|---|
| | Conc. (ng/ml) | /Ref. | Conc. (ng/ml) | /Ref. | Conc. (ng/ml) | /Ref. |
| 3 freeze/thaw cycles | 82.8 | −3% | 851 | −3% | 2131 | −1% |
| 2 freeze/thaw cycles | 90.4 | 6% | 862 | −2% | 2137 | −1% |
| 1 freeze/thaw cycle | 85.4 | 0% | 875 | −1% | 2153 | 0% |

Example 4: Calibration Curve

Figure 1:
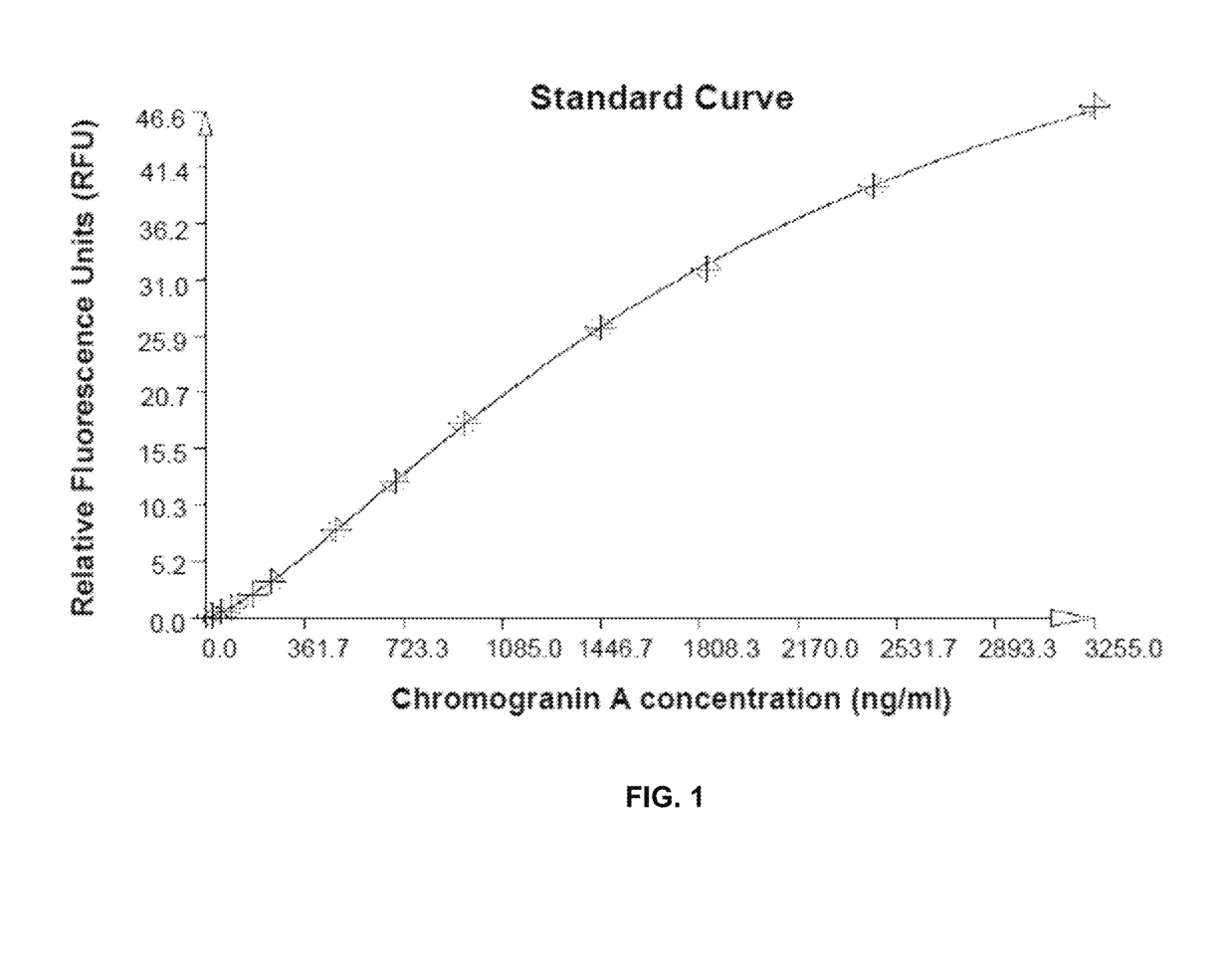
FIG. 1 shows a standard curve employing different concentrations of Chromogranin A using the immunoassay method of Example 4.

FIG. 1 shows the dose response curve for the (537/H2-Cryptate; 541/E2-Alexa Fluor647®) KRYPTOR assay using Time Resolved Amplified Cryptate Emission (TRACE) technology. Based on the calibration curve, the direct reading range for (537/H2-Cryptate; 541/E2-Alexa Fluor647®) KRYPTOR assay is defined up to 3000 ng/ml.

Figure 2:
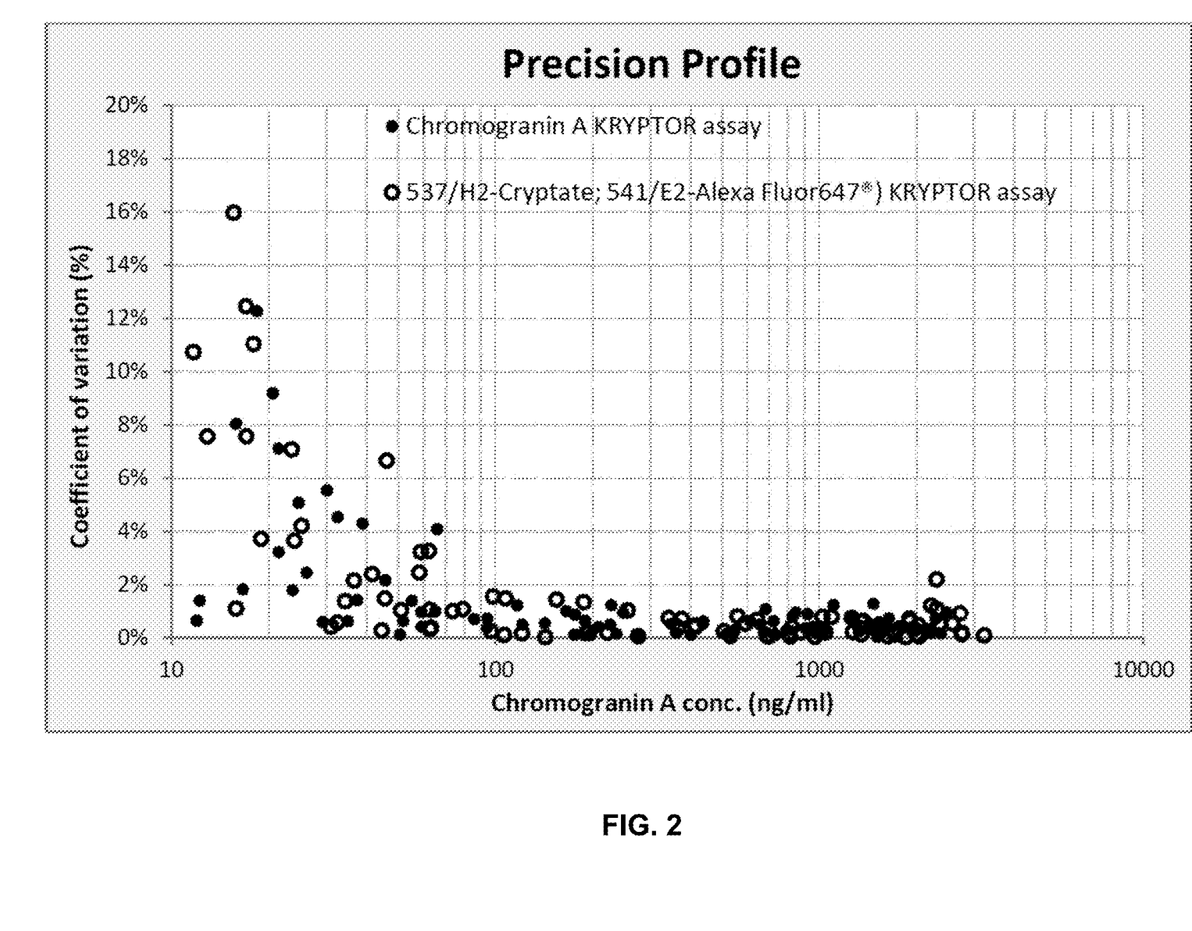
FIG. 2 shows the precision profile of an immunoassay of the present invention as compared to the prior art KRYPTOR Chromogranin A assay (Thermo Fisher Scientific B.R.A.H.M.S GmbH, Hennigsdorf, Germany) (Example 5).

Example 5: Precision Profile and Sensitivity 91 samples (24 from healthy donors and 67 pathological samples) were measured in parallel using the 537/H2 and 541/E2 antibodies in the conditions described above and the prior art KRYPTOR Chromogranin A assay (Thermo Fisher Scientific B.R.A.H.M.S GmbH, Hennigsdorf, Germany). Measurements were performed in duplicates and the coefficient of variation of each duplicate was plotted against Chromogranin A concentration on the same graph. The precision profile are equivalent for both assays. Functional assay sensitivity claimed for the KRYPTOR Chromogranin A assay is 9.04 ng/ml; with (537/H2-Cryptate; 541/E2-Alexa Fluor647®) KRYPTOR assay, the functional assay sensitivity estimated for a 10% CV is 13.1 ng/ml.

The invention claimed is:

1. A method for the therapy control of a neuroendocrine tumour or prostate cancer in a subject comprising:
  (a) determining the presence and/or absence or the level of Chromogranin A or a fragment thereof in a sample from said subject using an immunoassay method comprising the steps of:
    (i) contacting said sample with a first antibody or an antigen-binding fragment thereof specific for Chromogranin A, and
    (ii) a second antibody or an antigen-binding fragment thereof specific for Chromogranin A,
    wherein the first antibody is produced by the hybridoma cell line 537/H2 deposited as DSM ACC3231 or is an antigen-binding fragment of the antibody produced by the hybridoma cell line 537/H2 deposited as DSM ACC3231;
    or the second antibody is produced by the hybridoma cell line 541/E2 deposited as DSM ACC3232 or is an antigen-binding fragment of the antibody produced by the hybridoma cell line 541/E2 deposited as DSM ACC3232;
    or the first antibody is produced by the hybridoma cell line 537/H2 deposited as DSM ACC3231 or is an antigen-binding fragment of the antibody produced by the hybridoma cell line 537/H2 deposited as DSM ACC3231, and the second antibody is produced by the hybridoma cell line 541/E2 deposited as DSM ACC3232 or is an antigen-binding fragment of the antibody produced by the hybridoma cell line 541/E2 deposited as DSM ACC3232;
    under conditions allowing for the formation of a ternary complex between Chromogranin A and the two antibodies or antigen-binding fragments or derivates thereof,
  (c) detecting the binding of the two antibodies or antigen-binding fragments or derivates thereof to Chromogranin A;
  (d) adjusting the therapeutic treatment of the subject.

2. The method of claim 1, wherein the sample is derived from a bodily fluid or tissue of said subject.

3. The method of claim 2, wherein the bodily fluid is selected from blood, serum, plasma and urine.

4. The method of claim 1, wherein the assay is performed in homogeneous phase or in heterogeneous phase.

5. The method of claim 1, wherein one of the antibodies is labeled and the other antibody is bound to a solid phase or can be bound selectively to a solid phase.

6. The method of claim 1, wherein the first and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to the Chromogranin A to be detected, a measurable signal which permits detection of the resulting sandwich complexes in the measuring solution is generated.

7. The method of claim 6, characterized in that the labelling system comprises rare earth cryptates or chelates in combination with a fluorescent or chemiluminescent dye.

8. The method of claim 7, wherein the fluorescent or chemiluminescent dye is of the cyanine type.

* * * * *